July 2, 1940. C. MALLERIN Plant Pat. 409
ROSE PLANT
Filed March 5, 1940
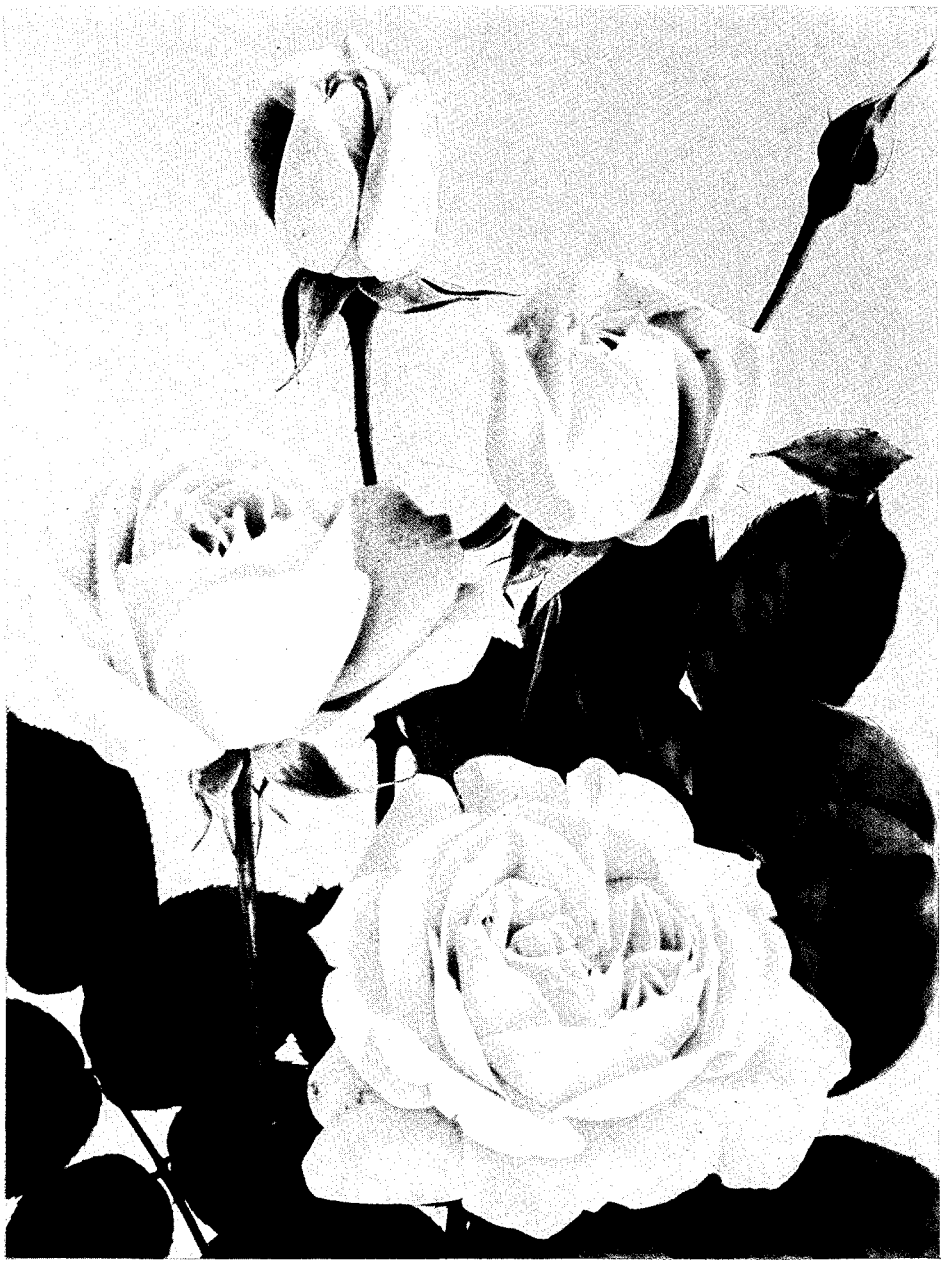
Inventor
C. Mallerin
By Robb & Robb
Attorneys Patented July 2, 1940

Plant Pat. 409

UNITED STATES PATENT OFFICE

409

ROSE PLANT

Charles Mallerin, Varces, par Pont de Claix, France, assignor to The Conard-Pyle Company, West Grove, Pa.

Application March 5, 1940, Serial No. 322,409

1 Claim. (Cl. 47—61)

The present invention relates to a new and distinct variety of rose plant of the Pernetiana class, the result of a definite effort to produce a rose of vigorous growth, abundant foliage, and distinctive coloring.

This objective was reached in this new rose which not only possesses excellent qualities of vigor, growth, abundant foliage, and excellent vegetative potential, but also the characteristic of production in good degree of blossoms and buds entirely new and different, particularly with respect to the shading and colors that represent an altogether new tone, from any known rose.

The following is a detailed description of this new rose, the color terminology employed therein being in accord with Ridgway's Color Standard.

Type: Half hardy; bush, outdoor; seedling; for cut flowers and garden decoration.

Class: Pernetiana.

Parentage:

*Seed parent.*—Lucy Nicolas.

*Pollen parent.*—Brasier.

Propagation: It holds its distinguishing characteristics through succeeding propagations by budding.

*Flower*

Locality where grown: West Grove, Pennsylvania.

Flowers borne: Singly and several to stem on strong, medium length stems.

Quantity of bloom: Moderate, outdoors.

Continuity: Intermittent.

Fragrance: Moderate; spicy, resembling sweet clover.

Bud:

*Peduncle.*—Medium long, medium heavy, erect, stiff; Parrot Green to Grass Green, Plate VI; few medium rough, Sanford Brown, Plate II, prickles.

*Before calyx breaks.—Size*—medium. *Form*—ovoid with a conspicuous neck; with foliaceous appendages on the surface of the bud; with slender foliaceous parts extending beyond the tip of the bud equal to one-fourth or more of its length.

*As calyx breaks.—Color*—Brazil Red, Plate I.

*As first petal opens.—Size*—medium large. *Form*—ovoid. *Color:* outside—Peach Red washed Brazil Red, Plate I; inside—Scarlet Red, Plate I, with wash of Flame Scarlet, Plate II. *Opening*—opens up well.

Bloom:

*Size, when fully open.*—Medium, 3½ inches to 4 inches.

*Petalage.*—Double, from 25 to 35 petals; arranged regularly.

*Form.*—High center at first; becoming cupped; petals remaining at first loosely rolled outward; becoming later, at maturity, loosely rolled outward.

Petals: Thick, leathery, with inside satiny; outside dull satin.

*Shape.*—Outside—both round and obovate; some are scalloped with one notch. Intermediate—obovate, scalloped with one notch. Inside—obovate, scalloped with one notch.

This description of a newly opened flower was made from a rose grown outdoors, in September, 1939, at West Grove, Pennsylvania:

*Color.*—Outside petal: outside surface—Light Salmon Orange, Plate II, washed Peach Red, Plate I. Intermediate petal: outside surface—Light Salmon Orange, Plate II, washed Peach Red, Plate I. Inner petal: outside surface—Light Salmon Orange, Plate II, washed Peach Red, Plate I.

This description was made from a rose that was open for three days, outdoors, in September, 1939, at West Grove, Pennsylvania:

*Color.*—Outside petal: outside surface—Light Cadmium, Plate IV; inside surface—Alizarine Pink, Plate XIII. Inside petal: outside surface—Pale Orange Yellow, Plate III; inside surface—Alizarine Pink, Plate XIII.

*General color effect.*—Newly opened flower—Bittersweet Orange to Grenadine, Plate II. Three days open—Alizarine Pink, Plate XIII.

*Behavior.*—Persist, Alizarine Pink, Plate XIII; burns during hot weather.

*Flower longevity.*—On bush in garden, five days in September; cut roses grown outdoors, three days in September.

*Productive organs*

Stamens: Medium number; arranged regularly about pistils.

Filaments: Medium length; Cadmium Yellow, Plate III; a few without anthers.

Anthers: Small; Cadmium Yellow, Plate III; open at various times.

Pollen: Abundant; Deep Chrome, Plate III.

Pistils: Medium number.

Styles: Uneven; medium length; medium heavy; bunched, columnar.
Stigma: Buff Yellow, Plate IV.
Ovaries: All enclosed in calyx.
Sepals: Moderately long.

*Plant*

Foliage:

*Leaves.*—Compound of three, five, seven; normal; large; leathery.

*Leaflets.*—Ovoid with apex acute, base obtuse, margin simply serrate.

*Color.*—*Mature:* upper surface—Dark Elm Green, Plate XVII; under surface—Bice Green, Plate XVII, with Old Rose (Plate XIII) veins. *Young:* upper surface—Grass Green, Plate VI; under surface—Parrot Green, Plate VI.

*Rachis.*—(The supporting stem of the compound leaf), heavy. Upper side—Grooved, hairy. Under side—Sparsely prickly.

*Stipules.*—Medium length; medium wide, with short points turning out at an angle of more than 45°, recurved toward the stipules.

*Disease.*—Subject to blackspot.

Growth:

*Habit.*—Bushy, upright, much branched.

*Growth.*—Free, vigorous.

*Canes.*—Heavy.

*Main stems.*—Grass Green, Plate VI. *Thorns*—several; medium length; hooked downward, with short narrow base. *Prickles*—none. *Hairs*—none.

*Branches.*—Grass Green, Plate VI. *Thorns*—several; medium length; hooked downward, with short narrow base. *Prickles*—none. *Hairs*—none.

*New shoots.*—Grass Green, one side, Plate VI; Mahogany Red, other side, Plate II. *Thorns*—several; long; hooked downward, with short narrow base. *Prickles*—none. *Hairs*—none.

I claim:

A new and distinct variety of rose plant characterized as to novelty by its vigorous growth, abundance of foliage, and production of blossoms and buds new in shading and colors which vary in the different stages of development of the blossom, substantially as shown and described.

CHARLES MALLERIN.